United States Patent [19]

D'Silva et al.

[11] Patent Number: 5,889,587
[45] Date of Patent: Mar. 30, 1999

[54] MOBILE INDUCTIVELY COUPLED PLASMA SYSTEM

[75] Inventors: Arthur P. D'Silva; Edward J. Jaselskis, both of Ames, Iowa

[73] Assignee: Iowa State University Research Foundation, Ames, Iowa

[21] Appl. No.: 117,242

[22] Filed: Sep. 3, 1993

Related U.S. Application Data

[63] Continuation of Ser. No. 770,524, Oct. 3, 1991, abandoned.

[51] Int. Cl.⁶ ........................................... G01J 3/30
[52] U.S. Cl. .............................................. 356/316
[58] Field of Search .................... 356/315–316, 356/318–319, 36

[56] References Cited

U.S. PATENT DOCUMENTS

| | | | |
|---|---|---|---|
| 3,521,959 | 7/1970 | Fassel et al. | 356/316 |
| 4,598,577 | 7/1986 | Jowitt et al. | 356/36 |
| 4,802,761 | 2/1989 | Bowden et al. | 356/301 |
| 4,986,658 | 1/1991 | Kim | 356/318 |
| 5,085,499 | 2/1992 | Griffin et al. | 356/316 |
| 5,104,391 | 4/1992 | Ingle et al. | 356/73.1 X |

FOREIGN PATENT DOCUMENTS

| | | | |
|---|---|---|---|
| 0200446 | 9/1986 | Japan | 356/316 |

OTHER PUBLICATIONS

Brewer et al., "Studies of Aerosols Generated by Electrically Vaporized Thin Films for ICP–AES", Applied spectroscopy, vol. 44, No. 3, 1990, 356/316.

Jin et al., "An Efficient and Inexpensive Ultrasonic Nebulizer for Atomic Spectroscopy", Applied spectroscopy, vol. 44, No. 2, 1990, Article of 46 Photonics Spectra, June 1991.

*Primary Examiner*—K. P. Hantis
*Attorney, Agent, or Firm*—Schwegman, Lundberg, Woessner, and Kluth, P.A.

[57] ABSTRACT

A system for sampling and analyzing a material located at a hazardous site. A laser located remote from the hazardous site is connected to an optical fiber, which directs laser radiation proximate the material at the hazardous site. The laser radiation abates a sample of the material. An inductively coupled plasma is located remotely from the material. An aerosol transport system carries the ablated particles to a plasma, where they are dissociated, atomized and excited to provide characteristic optical reduction of the elemental constituents of the sample. An optical spectrometer is located remotely from the site. A second optical fiber is connected to the optical spectrometer at one end and the plasma source at the other end to carry the optical radiation from the plasma source to the spectrometer.

17 Claims, 5 Drawing Sheets

MOBILE INDUCTIVELY COUPLED PLASMA SYSTEM

The Instant Application is a continuation of Ser. No. 07/770,524, filed Oct. 3, 1991, now abandoned.

The invention was made with support under contract with the Department of Energy Contract No. W-7405-ENG-82. The Government has certain rights in the invention.

TECHNICAL FIELD OF THE INVENTION

This invention pertains generally to the field of material analysis, and more particularly to method and apparatus for acquisition of a material sample from a remote site and subsequent analysis of the sample.

TECHNICAL FIELD OF THE INVENTION

There is often the need for sampling and analysis of dangerous or hazardous materials, or materials located in hazardous environments. Examples include sampling and analyzing the condition of soil or water at hazardous waste sites (radioactive wastes, toxic chemical dumps or contaminated structures) or of molten metals in a manufacturing foundry. Conventionally, a sample of a hazardous waste is removed from the site and brought to a laboratory for analysis. The sample must therefore be carefully extracted, transported, handled and stored in order to assure the safety of the technicians carrying out the test, as well as the public. The expense and delay entailed in extracting, handling and storing such materials, as well as the health risks, have encouraged scientists to develop alternative testing approaches minimizing these disadvantages.

BACKGROUND OF THE INVENTION

The present invention provides a method and apparatus for sampling and analyzing hazardous materials proximate the site and such that a an absolute minimum of hazardous material need be released or removed from the site.

According to one aspect of the invention, a remotely controlled mobile cart positions a probe proximate to the sampling site. A high energy wavelength laser ablates the material, forming a cloud of micron-sized particles. The particles are drawn from the sampling site by an aerosol system which employs an inert gas, such as argon. The sample particles and argon gas aerosol are injected into an inductively coupled plasma (ICP) source, which produces electromagnetic radiation which can be analyzed with an optical spectrometer.

In one embodiment, the laser source is located in a van or truck remote from the cart, with the laser beam from the source carried to the probe over an optical fiber. The inductively coupled plasma source is located on the mobile cart, with its optical output being carried over another optical fiber to an optical spectrometer located in the van or truck, from which the material analysis is obtained. In another embodiment, the laser and spectrometer are located on the cart.

The present invention also employs several unique probe structures which isolate the sampling site from the outside environment, ensuring that only the material ablated by the laser radiation is carried to the inductively couple plasma system (ICP) through the aerosol transport system. A special ceramic probe tip is employed to extract samples from molten materials.

Because length over which the aerosol system can carry the ablated sample, another embodiment collects the ablated sample on a filter media, which is taken to a remote site for analysis using the inductively coupled plasma system discussed above.

Finally, an ultrasonic or direct injection nebulization technique is used instead of the laser to produce aerosol particles from liquid materials at the sampling site to be analyzed by the ICP.

DETAILED DESCRIPTION OF THE PREFERRED EMBODIMENT

Figure 1:
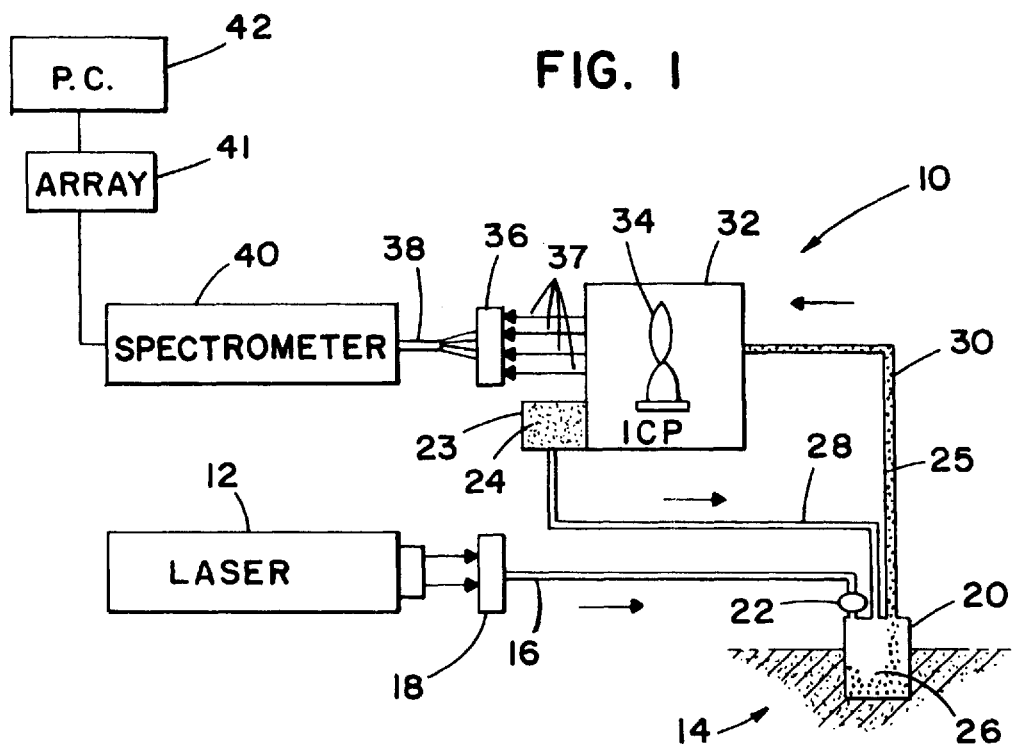
FIG. 1 provides a schematic illustration of the mobile inductively coupled plasma system of the present invention.

FIG. 1 provides a simplified schematic illustration of the mobile inductively coupled plasma system 10 of the present invention. Laser radiation from an ultraviolet laser 12 is directed to the sampling site 14 through fused silica fiber rod optics 16. Preferably, the laser provides continuous or pulsed, fixed wavelength laser radiation at at least three different wavelengths, 1064 nm, 532 nm, and 355 nm. These wavelengths are chosen to provide a range of energies as materials to be analyzed have different absorption characteristics at different wavelengths. Since current optical fibers are subject to damage at wavelengths below 350 nm and power levels of $10^8$ watts/$cm^2$/sec., it is best to utilize laser wavelengths above 350 nm. These constraints will change with the availability of better optical fibers. As most materials absorb optical radiation in the ultraviolet, ablation is more efficiently carried out at wavelengths below 400 nm. The Lumonics Dye Laser (Hyper-Dye 300) pumped by the Lambda Physik Excimer Laser (model EMG102MSC) is known to provide laser beams suitable for use in the present invention, although the preferred system for field operation is the solid state YAG laser.

A laser focusing system 18 is provided to focus the laser output onto the optical fiber 16, without overloading it. C Technologies fiber optics cable model SRA-6-1-20-01 is known to be suitable for carrying the laser radiation to a probe 20, provided no more than $10^8$ watts/$cm^2$/sec. is applied to the head end of the fiber. As noted above, power levels in excess of this can damage the fiber. Focusing system 18 may include a filter to narrow the laser beam and reduce the power actually received by the optical fiber and a series of lenses to focus the laser radiation onto the end of the optical fiber.

As will be discussed in more detail below with respect to FIG. 3, the probe 20 has optics 22 for focusing the laser radiation from the fiber 16 on the material to be sampled 14. The probe 20 is generally constructed of aluminum, but other materials may be preferable to contend with different environmental conditions. An argon gas source 23 supplies argon gas 24 to a probe sampling chamber 26 through an aerosol input line 28. The material ablated or sampled 25 by the laser radiation mixes with the argon 24 to form an aerosol which is drawn from the probe sampling chamber 26 through the aerosol output line 30 to the inductively coupled plasma (ICP) source 32. Argon 24 is the support gas for the ICP 32. The present invention employs an RF Plasma Products® inductively coupled argon plasma system.

As is conventional in the art, the aerosol is directed into the plasma source 34, through an input line (not shown) to the ICP 32. The energized sample particles are excited to provide characteristic optical reduction of the elemental constituents of the sample 25 in the form of electromagnetic radiation 37, which is focused by a lens 36 and thereby subsequently channeled through an ICP output optical cable 38 to a remotely located multi-channel or sequential optical spectrometer 40. To carry the optical output of the ICP 32 to the spectrometer 40, the preferred embodiment of the present invention employs Polymicro Technologies fiber optic bundle (model PTA-LEI0019FF-030-0DP), consisting of 19 separate 200 μm core diameter fibers arranged in a round-to-linear bundle. The Acton Research Corp. 0.5 meter spectrometer (model VM-505) equipped with a 2400 grooves/mm grating has been found suitable as the spectrometer. The optical radiation dispersed in the spectrometer is detected by a multichannel diode array detector 41. The EG&G Princeton Applied Research intensified diode array (model 1420) and diode array controller (model 1463) are known to be suitable for this purpose. Preferably, the IEEE output of the detector 41 is connected to a personal computer 42 or workstation whereby the output of the spectrometer 40 can be stored, enhanced, processed, analyzed, and displayed.

Figure 2:
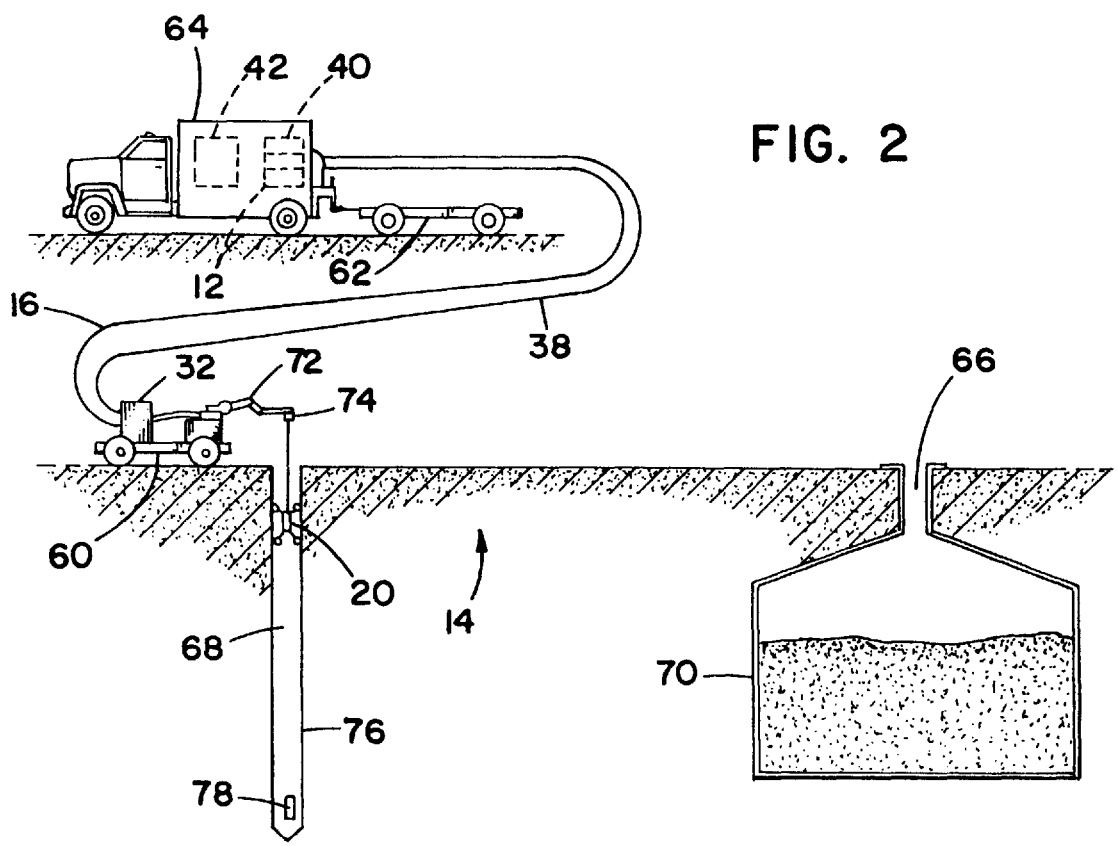
FIG. 2 illustrates one application of the mobile inductively coupled plasma system of the present invention for sampling soil at a hazardous waste site.

FIG. 2 illustrates one embodiment of the mobile inductively coupled plasma system 10 of the present invention. A remotely controlled mobile cart 60 is trailered on a trailer 62 behind a truck 64. The truck 64 contains a power source for operating the components of the system. In use, the truck 64 is positioned a distance from the toxic waste sampling site 14. The remotely controlled mobile cart 60 is then positioned proximate to the sampling site 14, for instance a sampling bore 68 adjacent to the toxic waste storage chamber 70, by direct visual reckoning or by use of video images relayed from a video camera (not shown) mounted on the cart 60. The controls for maneuvering cart 60 are located in the truck 64.

In the preferred embodiment of the present invention, the remotely controlled mobile cart 60 carries the ICP source 32, so that the ICP source is as close to the sampling site 14 as possible, thereby minimizing the distance the hazardous material needs to be transported in the aerosol output line 30 and to keep the hazardous material away from the operators positioned in the truck 64.

In the preferred embodiment, the aerosol tubes 28 and 30 are 0.25" in diameter, made of Teflon® or polyethylene material, and are pressurized to provide a gas flow of 1.0 liters/minute. The argon 24 is held under pressure in the argon source 23 to provide pressure to the system. The preferred embodiment of the present invention has achieved transportation of material samples 25 in the aerosol line 30 to a distance of 100 feet.

The laser source 12 and spectrometer 40 are located in the truck 64. As explained above with respect to FIG. 1, an optical fiber 16 carries the laser beam from the laser 12 to the probe 20, while a second fiber 38 carries the output of the ICP 32 to the spectrometer 40. Using the equipment specified herein, the laser beam can be carried up to 30 meters on the fiber 16. Similarly, fiber 38 can carry the output of the ICP 32 about 30 meters to the spectrometer 40.

The probe 20 is attached to a three-axis robot arm 72 mounted to the cart 60, which is also controlled remotely by the operator, preferably using images relayed from a video camera mounted on the platform or even on the probe itself. In the application shown in FIG. 2, the operator controls the robot arm 72 to position the probe 20 over the center of the sampling bore 68. The tubes 28 and 30 and fiber 16, a load-bearing cable 73, and other necessary electronic cables (not shown) are wound on a spool with a winch 74, which is remotely controlled to lower and raise the probe 20. In the preferred embodiment of the present invention, the sampling bore 68 contains a liner 76 (shown in more detail in FIG. 3), which can be a conventional pipe with a cut-out area, or window 78, through which access to the sampling site 14 is obtained.

The probe 20 is lowered into the sampling bore 68 until it is adjacent to the sampling window 78. The sampling thus proceeds with the operators at a safe distance from the sampling site 14. When sampling is completed, the probe 20 is withdrawn from the sampling bore 68 and the remotely controlled mobile cart 60 is returned to the trailer 62 for transportation to the next site. If any contamination has occurred, it is generally limited to the probe 20 or the immediate accessories (i.e., cables, etc.), allowing relatively easy clean-up. The sample 25 itself is incinerated in the ICP plasma source 34. If necessary, the probe 20 and accessories can be disposed of or destroyed and replaced at relatively low cost.

Figure 3:
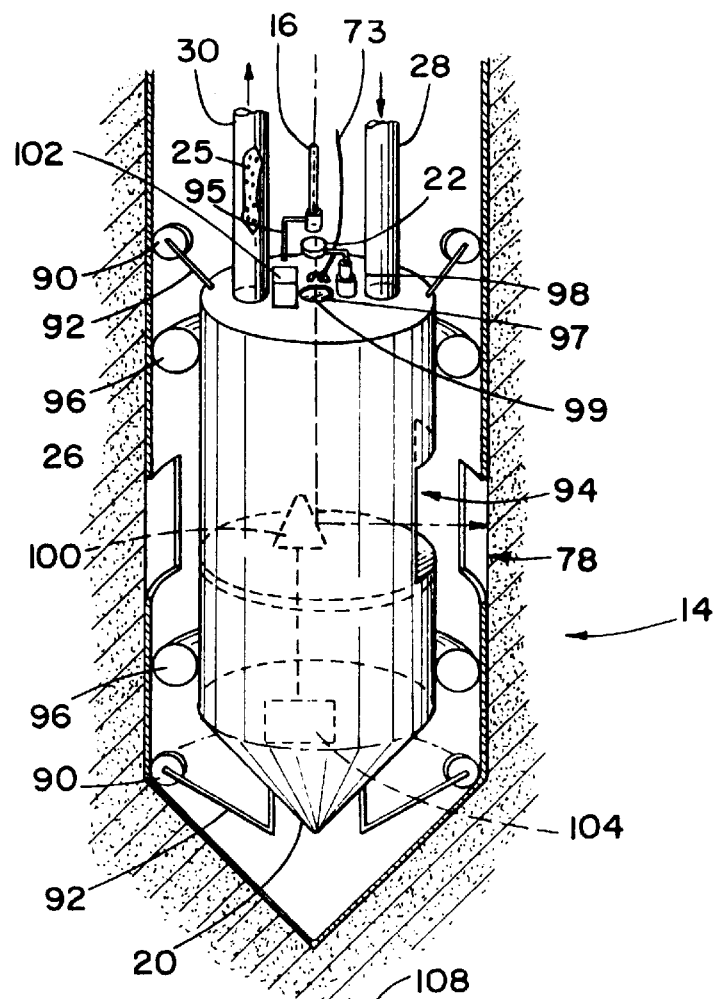
FIG. 3 is a detailed illustration of one type of probe of the preferred embodiment of the present invention.
Figure 4:
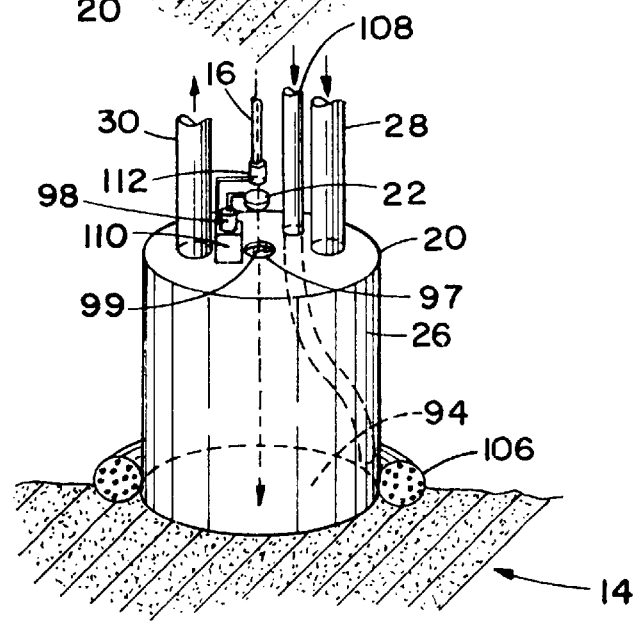
FIG. 4 illustrates an alternate sealing system for a probe which obtains samples from surface soil.
Figure 5:
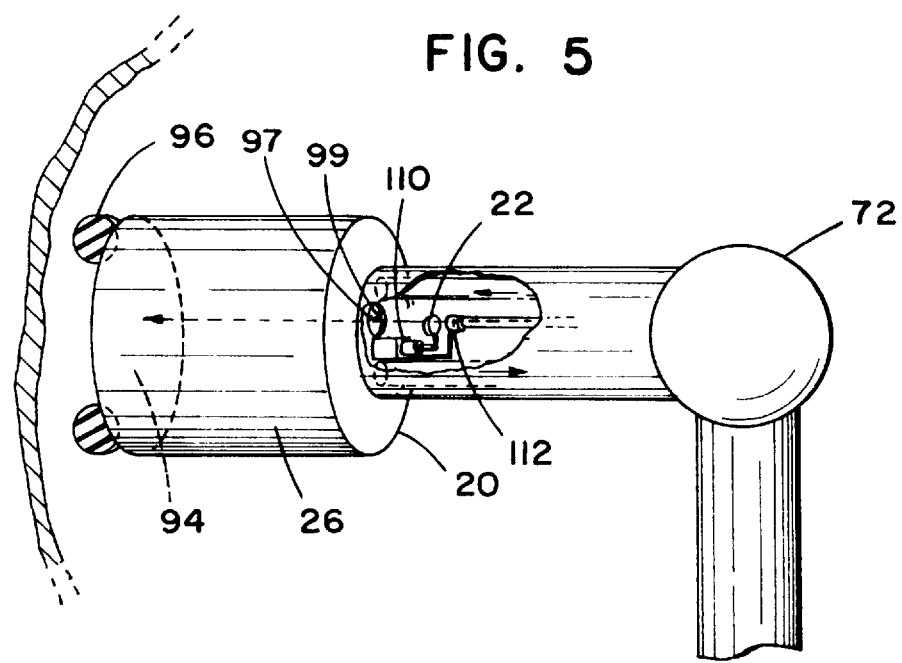
FIG. 5 illustrates another alternate sealing system for obtaining material samples from hard and uniform surfaces.
Figure 6:
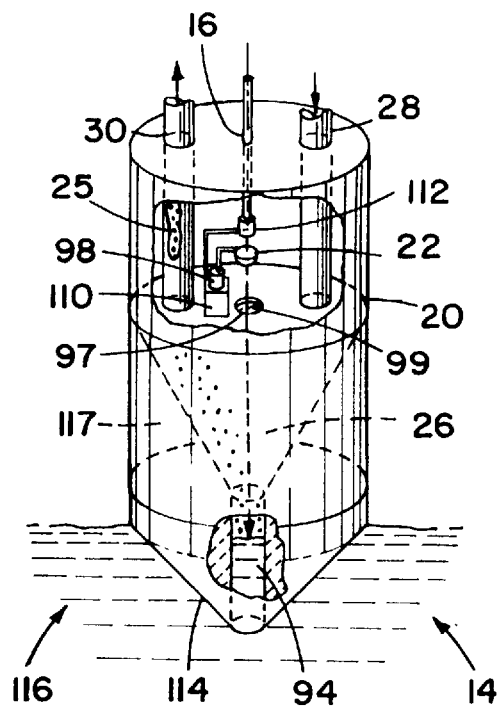
FIG. 6 is a detailed illustration of an alternate embodiment of the probe to be used to sample molten materials.
Figure 7:
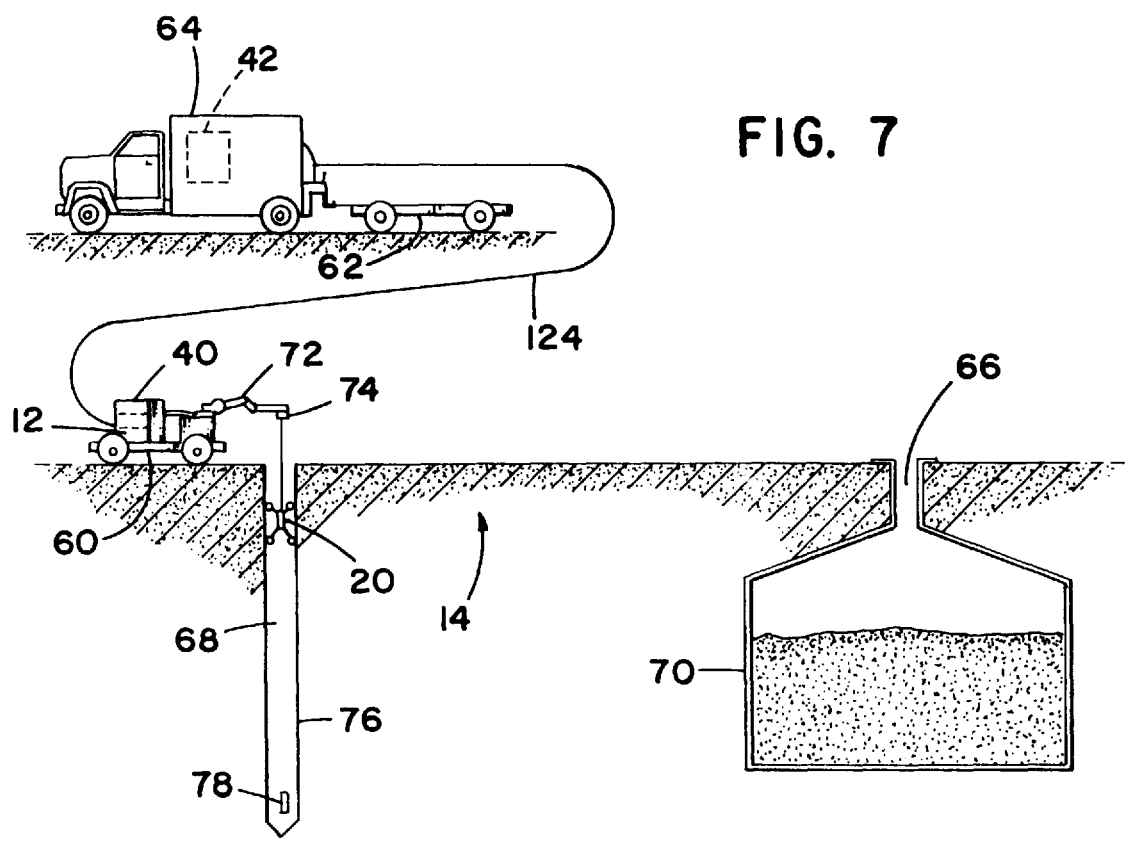
FIG. 7 illustrates an alternate embodiment of the mobile inductively coupled plasma system of the present invention where the laser and optical spectrometer are located on the mobile cart.
Figure 8:
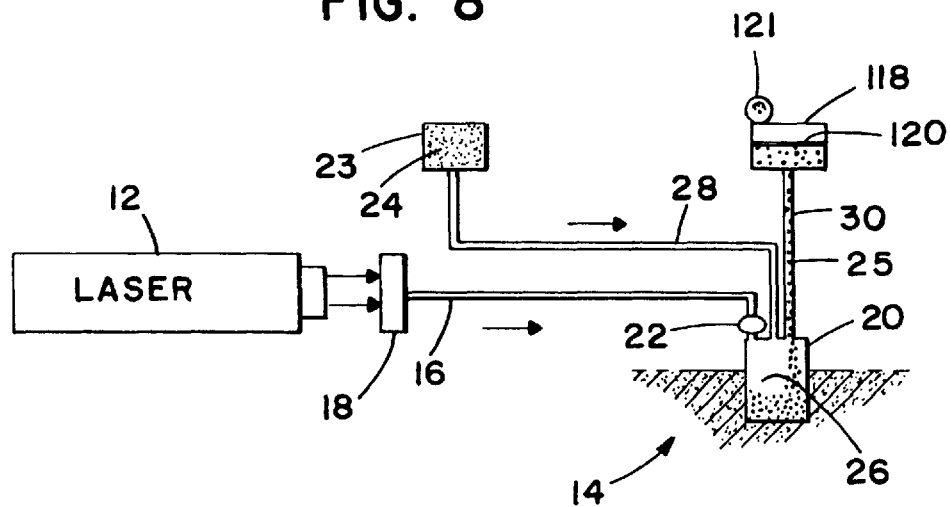
FIG. 8 is a schematic of an alternate embodiment of the present invention where the ablated sample is collected on a filter media.

FIG. 3 illustrates one embodiment of the sampling probe 20 of the present invention. Alignment wheels 90 are attached to the leading and trailing edges of probe 20 by flexible support members 92. The alignment wheels 90 allow the probe 20 to be lowered into the liner 76 without jamming. The probe 20 is lowered until a probe window 94 is aligned with the sampling window 78. Inflatable seals 96 are filled with compressed air from a pressurized source (not shown) so as to seal the sampling window 78 and the probe window 94 from the outside environment.

The sampling process entails focusing the laser radiation carried on the fiber 16 through a convex lens 22, which is located either inside or outside the probe sampling chamber 26, depending on the design chosen. The fiber 16 is secured to the probe 20 via bracket 95. In FIG. 3, the lens 22 is mounted outside the probe 20 on a telescoping support 98 with an integral stepper motor (not shown), which allows the convex lens 22 to be positioned to focus the laser beam on the material to be sampled 14, using stepper motor controller 102. An Oriel stepper motor (model 18512) and controller (model 20010) are known to be suitable for this purpose. The laser radiation passes through a transparent covering 99 over the opening 97 in probe 20, which isolates the sampling chamber 26 from the lens 22 and maintains the environmental integrity of the sampling process. A special rotating polygon mirror 100 at the base of the sampling chamber 26 reflects the beam onto the material, providing x and y axis rastering across the sampling site 14. Other approaches utilizing stepper motors configured to provide x–y and rotary motion can also be utilized. As will be discussed in more detail below, the operator monitors the intensity of the silicon spectra line generated by the optical spectrometer 40 to determine if the convex lens 22 is properly positioned to create the optimum focal length.

A variable speed motor 104 is remotely activated to rotate the polygon mirror 100, and direct the laser radiation in a raster scanning pattern across the sampling site 14. In the preferred embodiment of the present invention, scanning is performed at a rate of 5–10 millimeters per second. It is important that the laser radiation is sufficient to ablate the material to be sampled to create sufficiently small particles that can be transported through the aerosol output line 30. However, localized melting of the material should be avoided, since melting can change the composition of the sample material 25, leading to erroneous spectral analysis. Accordingly, the laser power (or wavelength) may need to be varied depending on the material being sampled. Further information on laser ablation is set forth in the paper entitled "Laser Vaporization in Atomic Spectroscopy," by H. K. Dittrich and R. Wennrich, *Prog. Analyt. Spectrosc.,* 7, 139–198 (1984), the entire contents of which are hereby incorporated by reference herein.

Argon 24 is forced into the probe sampling chamber 26 through the aerosol input line 28. The ablated sample particles 25 become mixed with the argon gas 24 and are subsequently drawn from the probe sampling chamber 26 through the aerosol output line 30. As discussed above, the aerosol output line 30 directs the mixture of argon gas 24 and sample particles 25 to the ICP plasma source 34.

As soon as the laser 12 is activated to initiate sampling of a soil, the operator observes the spectrometer 40 output for signs of silicon, since silicon is present in virtually all soils. The position of the convex lens 22 in the sampling chamber 26 is adjusted, by stepping the telescoping support 98, until the intensity of the silicon line in the spectrometer is maximized. At this point, the focal length of the laser radiation is correctly adjusted to focus the beam on the material to be sampled. Rastering can be performed during adjustment of the focus or initiated immediately after focus is achieved. By rastering, localized melting can be avoided and a relatively large sample area can be covered. In the preferred embodiment, a sample area of 1 $inch^2$ is covered during rastering. When sampling is completed, the air is released from the seals 96 and the probe 20 is withdrawn from the sampling bore 68 by the three axis robot arm 72.

FIG. 4 illustrates an alternative configuration for sealing the probe 20 against the material to be sampled. The probe 20 of FIG. 4 is not shown attached to the cable 73 or the 3-axis robot arm 72 since some applications of the present invention will permit the probe 20 to be placed on the sampling site 14 manually. For example, where the material to be sampled is not toxic to humans. However, it will be understood by those skilled in the art that any of the probe configurations disclosed herein can be attached to a variety of devices for locomotion.

Like the embodiment of FIG. 3, a convex lens 22 and telescoping support 98 are mounted to the top of the probe 20 for focusing the laser radiation through the transparent covering 99 to the correct focal length. Preferably, the telescoping unit 98 is mounted to a moveable base 110 with x and y degrees of freedom, controlled by stepper motor and controller 102 (not shown). The Oriel stepper motor (model 18512) and controller (model 20010) discussed above are known to be suitable for this purpose. The free end of the fiber 16 is fixed relative to the base 110 using an armature 112, to keep it aligned over the lens as the base 110 moves. The moveable base 110 is remotely activated to direct the laser radiation in a raster scanning pattern across the sampling site 14.

A perforated elastic tubular member, or seal, 106 is placed around the outside perimeter of the probe window 94. The perforated seal 106 is preferably constructed of polyethylene foam or some other suitably porous material. Water is provided by a water line 108 to moisten the perforated seal 106 and soil surrounding the sampling site 14. The moisture operates to seal the sampling chamber 26 from the outside environment.

FIG. 5 illustrates yet another method to seal the probe 20 against the material to be sampled. The probe again requires a similar convex lens 22 and telescoping support 98 for focusing the laser radiation onto the sampling site 14. The moveable base 110 is remotely activated to move the end of the fiber 16 in a raster scanning pattern. The probe 20 is attached to the 3-axis robot arm 72 so that it can be positioned in a variety of angles. An inflatable seal 96 is provided around the probe window 94, which is filled with compressed air during the sampling process. The configuration of FIG. 5 is intended primarily for sampling on substantially smooth surfaces, such as walls and ceilings of buildings. However, a variety of methods are available for isolating the probe chamber 26 from the outside environment during sampling.

FIG. 6 illustrates the use of the mobile inductively coupled plasma system of the present invention for sampling molten metals and alloys 116. The probe 20 is constructed similar to that disclosed in FIGS. 4 and 5. The convex lens 22 and telescoping support 98 are mounted inside the probe 20 to protect them from heat. As discussed above, the telescoping unit 98 is mounted to a moveable base 110 with x and y degrees of freedom to move the free end of the fiber 16 in a raster scanning pattern across the sampling site 14.

A thermally resistant hollow ceramic probe tip 114 is mounted to the sampling end of the probe 20. The ceramic tip 114 is used to penetrate the slag layer on the top of the molten metal 116, thereby exposing the molten metal below. The water lines 108 provides cooling liquid to a cooling chamber 117, which is located between the optics 22 and the ceramic probe tip 114. Sampling occurs in the sampling chamber 26, as discussed in detail above.

FIG. 7 illustrates an alternate embodiment of the mobile inductively coupled plasma system of the present invention where the laser 12 and optical spectrometer 40 are located on the mobile cart 60, along with the diode array 41. The electrical output signals from the diode array 41 are carried by cable 124 to the computer 42 in the truck 64.

FIGS. 8 and 9 illustrate yet another embodiment of the mobile inductively couple plasma system of the present invention. As discussed above, the aerosol system (argon gas source 23 and argon gas 24) of the present invention has achieved transportation of material samples 25 in the aerosol line 30 to a distance of 100 feet. However, the toxic or radioactive nature of some sampling sites 14 may require that the sample be transported more than 100 feet in the aerosol, or it may not be possible for the material to be easily carried on the aerosol. FIG. 8 illustrates a system were the ablated sample 25 is carried from the sampling chamber 26 through aerosol output line 30 to a filter media chamber 118 containing a filter media 120, which accumulates particles of the sample 25. The filter paper 120 must generally have sub-micron sized pores to insure capturing sufficient sample 25 material. However, the pore size of the filter paper may vary depending on the material being sampled.

Argon gas 24 can be allowed to escape from the top of the filter paper chamber 118. A meter 121 is located proximate to the top of the filter paper chamber 118 to monitor the quantity of argon gas 24 present. As the pores of the filter media 120 become clogged with sample material 25, the quantity of argon gas 24 flowing through the filter media 120 will decrease, with a corresponding decrease in the quantity of argon 24 detected by the meter 121. When the quantity of argon gas 24 detected by the meter 121 drops to a predetermined level, sampling is terminated.

Figure 9:
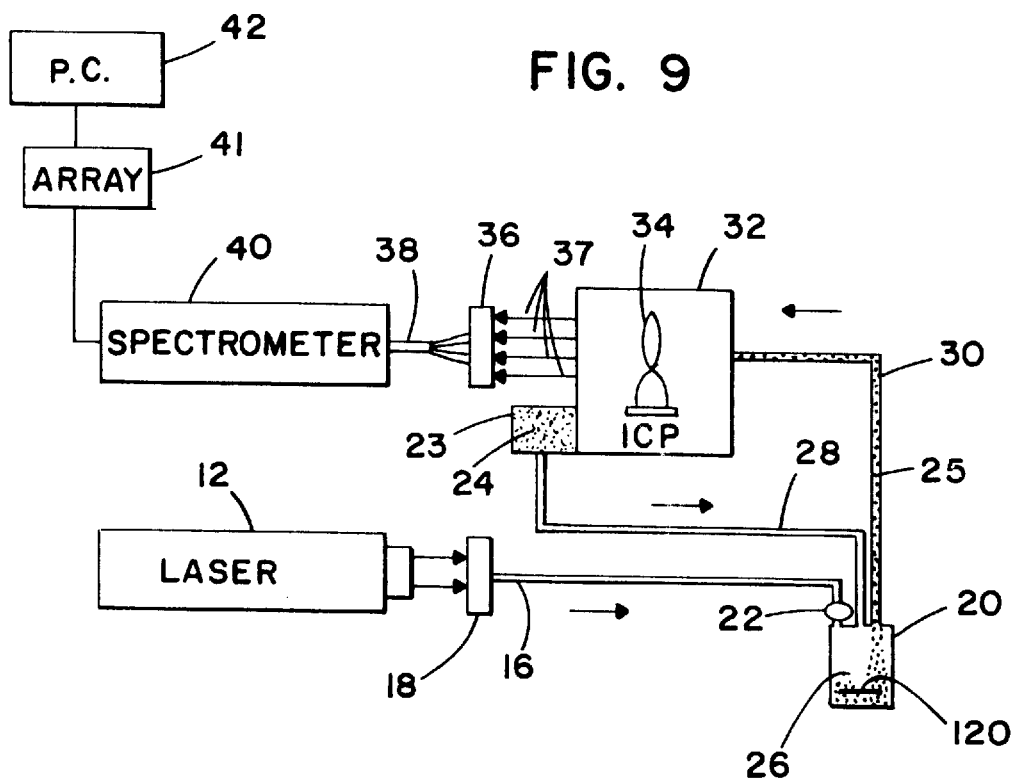
FIG. 9 is a schematic of an alternate embodiment of the present invention where the filter media is subject to ablation for purposes of analyzing the sample.

The filter media is then removed from the toxic site for analysis. FIG. 9 illustrates a laser ablation system for analyzing the sample 25 collected on the filter media 120. The filter media 120 is placed in the probe 20, where it is subject to the laser ablation process discussed above.

Figure 10:
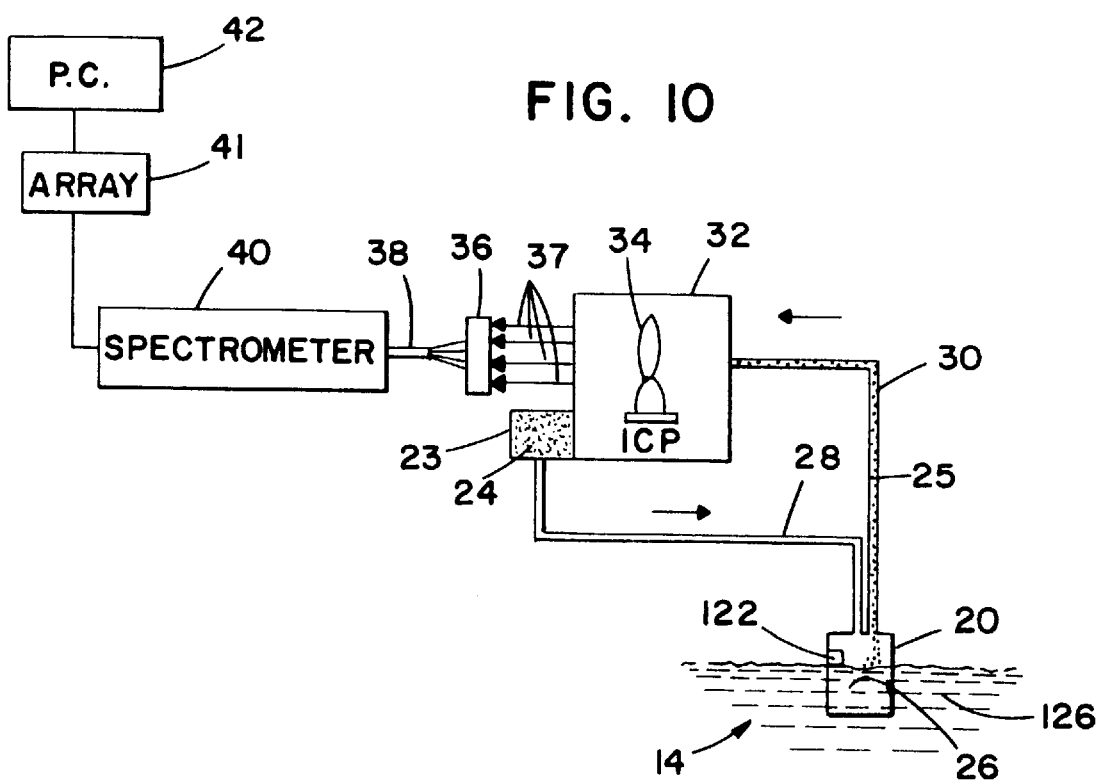
FIG. 10 is a schematic of the mobile inductively coupled plasma system of the present invention for use in sampling and analyzing liquid materials.

FIG. 10 illustrates the use of an ultrasonic nebulizer to produce aerosol 25 from liquid material 126. In principle, when ultrasonic waves from a transducer 122 of sufficient frequency and amplitude are produced, a capillary wave action is induced in a liquid medium 126, causing the ejection of aerosol droplets from the liquid surface. The droplets, the dimensions of which are dependent on the ultrasonic frequency and physical properties of the liquid, can be produced with micron sized diameters. By synchronizing the transducer 122 frequencies and focusing the ultrasonic waves to a single point, a wave pattern should be generated with an amplitude sufficient to provide the quantities of sample 25 required for ICP 32 analysis. A low frequency, high power, ultrasonic stephorn generator known to be suitable for the present embodiment is disclosed by Fassel and Dickinson, *Anal. Chem.* 40, 1968, 247; and in U.S. Pat. No. 3,521,949. Once a representative aerosol sample 25 is generated, it mixes with the argon 24 and is transported to ICP 32 for analysis.

The nebulized liquid material 126 is drawn through the aerosol output line 30 to the ICP 32. Sample analysis proceeds as discussed in detail above.

It will be understood that the present invention is not limited to the examples discussed above, but may be changed or modified without departing from the spirit or scope of the invention.

We claim:

1. A system for sampling and analyzing a material located at a hazardous site, the material having a surface and elemental constituents, comprising:
    a portable sampling probe;
    a laser source located remote from the sampling probe and producing a laser beam directed onto the surface of the material through an optical fiber, the optical fiber having two ends, a first end proximate said laser source to receive said laser beam and a second end mounted to said sampling probe so that when positioned by movement of said probe proximate the material at the hazardous site, the laser beam emitted from the second end ablates a sample of the material;
    an inductively coupled plasma source remotely located from the material where the sample is ablated;
    an aerosol transport system for transporting the sample from the material to the inductively coupled plasma source wherein the sample is excited by the plasma source to provide an output emission characteristic of the elemental constituents of the sample; and
    an elemental constituent detector remotely located from the inductively coupled plasma source and receiving the output emission of said inductively coupled plasma source, an output of the detector providing an indication of the elemental constituents of the sample.

2. The system of claim 1 further wherein said sampling probe comprises:
    a housing defining a sampling chamber in communication with said aerosol transport system, the chamber having an opening for receiving the sample; and
    a lens on an adjustable support mounted to the housing, the lens interposed between said second end of said first optical fiber and the material to focus and direct said laser beam through said opening onto the material, so that said aerosol transport system carries the sample to the plasma source.

3. The system of claim 1 further wherein the sampling probe comprises a housing defining a sampling chamber in communication with said aerosol transport system, the chamber having an opening for receiving the sample, whereby said aerosol transport system carries the particles to the plasma source.

4. The system of claim 3 further including rastering means for rastering said laser beam across the material.

5. The system of claim 2 further including seal means attached to the housing proximate to said opening for engagement with the surface of the material to be sampled for substantially isolating said sampling chamber and the material from the outside environment during sampling.

6. The system of claim 3 further wherein the opening is defined on an end of said probe and the end of the probe is constructed of a thermally resistant material.

7. The system of claim 1 wherein a sample of particles is ablated from the material by the laser, and wherein the detector is an optical spectrometer.

8. The system of claim 1 further where the sampling probe includes a filter for collecting the sample of the material; and
    the detector is an optical spectrometer in optical communication with said inductively coupled plasma source to receive said electromagnetic radiation.

9. The system of claim 1, further comprising a second optical fiber having a first end proximate the inductively coupled plasma source for collecting the output emission and a second end proximate the elemental constituent detector for delivering the output emission to the elemental constituent detector.

10. A method for sampling and analyzing a material located at a hazardous site, the material having a surface and elemental constituents, comprising the steps of:
    a) positioning a portable sampling probe proximate the surface of the material at the hazardous site;
    b) directing laser radiation from a laser source located remote from the probe onto the surface of the material through a first optical fiber, the first optical fiber having two ends, a first end coupled to said laser source and a second end mounted to the portable sampling probe, the laser radiation ablating a sample from the material;
    c) transporting the sample through an aerosol transport system from said probe to a remotely located inductively coupled plasma source; and
    d) exciting the sample in the plasma source to provide an emission characteristic of the elemental constituents of the sample.

11. The method according to claim 10 further wherein the emission is electromagnetic radiation and further including the step iof applying the emission to an elemental constituent detector located remote from the inductively coupled plasma source.

12. The method of claim 11 further including the step of applying said emission from said plasma source to said detector through a second optical fiber.

13. The method of claim 10 further including the step if raster scanning the surface of the material with the laser radiation.

14. The method of claim 10 further wherein the probe has a sampling chamber and including the step of substantially isolating said sampling chamber and the material from the outside environment during sampling.

15. The method of claim 10 further including the step of providing a thermally resistant tip on the probe for sampling molten metal.

16. A method for sampling and analyzing a material located at a hazardous site, the material having a surface and elemental constituents, comprising the steps of:

a) positioning a portable sampling probe proximate the surface of the material at the hazardous site;

b) directing laser radiation from a laser source located remote from the probe onto the surface of the material through an optical fiber, the optical fiber having two ends, a first end coupled to said laser source and a second end mounted to the portable probe, the laser radiation ablating a sample of the material;

c) collecting the sample in a filter mounted in the probe;

d) exciting the sample collected on said filter in an inductively coupled plasma source located remotely from the material to provide a characteristic emission of the elemental constituents of the sample; and e) applying said emission to an elemental constituent detector located remote from the inductively coupled plasma source.

17. The method of claim 16, further comprising the steps of:

a) ablating the sample collected on the filter using laser radiation; and b) transporting the ablated sample to the inductively coupled plasma source using an aerosol transport system.

* * * * *